United States Patent [19]

Dolgin et al.

[11] Patent Number: 5,071,426
[45] Date of Patent: Dec. 10, 1991

[54] SURGICAL SCALPEL WITH RETRACTABLE BLADE GUARD

[75] Inventors: Stuart Dolgin, 95 Belvedere Dr., Syossett, N.Y. 11791; Phillip Torbet, Upper Brookville, N.Y.

[73] Assignee: Stuart Dolgin, Syossett, N.Y.

[21] Appl. No.: 334,633

[22] Filed: Apr. 6, 1989

[51] Int. Cl.[5] ............................................. A61B 17/32
[52] U.S. Cl. ................................. 606/167; 30/151; 30/335
[58] Field of Search ............... 606/167, 172, 181, 182, 606/185; 30/162, 335, 151, 167, 286, 164; 128/751

[56] References Cited

U.S. PATENT DOCUMENTS

| | | | |
|---|---|---|---|
| 2,380,787 | 7/1945 | Pierce et al. | 30/220 |
| 3,905,101 | 9/1975 | Shepherd | 30/335 |
| 4,713,885 | 12/1987 | Keklak et al. | 30/335 |
| 4,735,202 | 4/1988 | Williams | 606/167 |
| 4,757,612 | 7/1988 | Peyrot | 30/151 |

*Primary Examiner*—C. Fred Rosenbaum
*Assistant Examiner*—William W. Lewis
*Attorney, Agent, or Firm*—Darby & Darby

[57] ABSTRACT

A scalpel is provided with a blade guard which is mounted for movement between a blade-guarded position and a blade-exposed position and an actuating mechanism for the blade guard is positioned in such a way that the fingers of the surgeon automatically engage the mechanism when the scalpel is held in its normal position of use. The actuating mechanism is coupled to the blade guard through a linkage assembly which causes the blade guard to move over a substantially greater distance than the distance which the surgeon's fingers move in operating the actuating mechanism. In a preferred embodiment, the blade guard slides over a linear path, the actuating mechanism comprises a tongue-like structure integral with the scalpel, and the linkage assembly comprises a plurality of pivotally interconnected lever arms. One of the lever arms is positioned so as to be captured in a detent mechanism when the blade guard is fully retracted to its blade-exposed position.

20 Claims, 4 Drawing Sheets

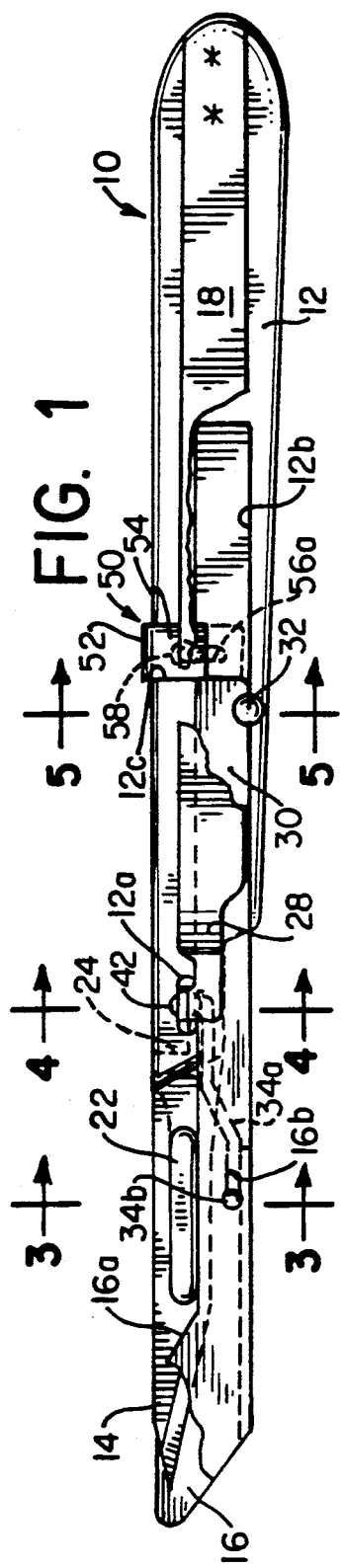
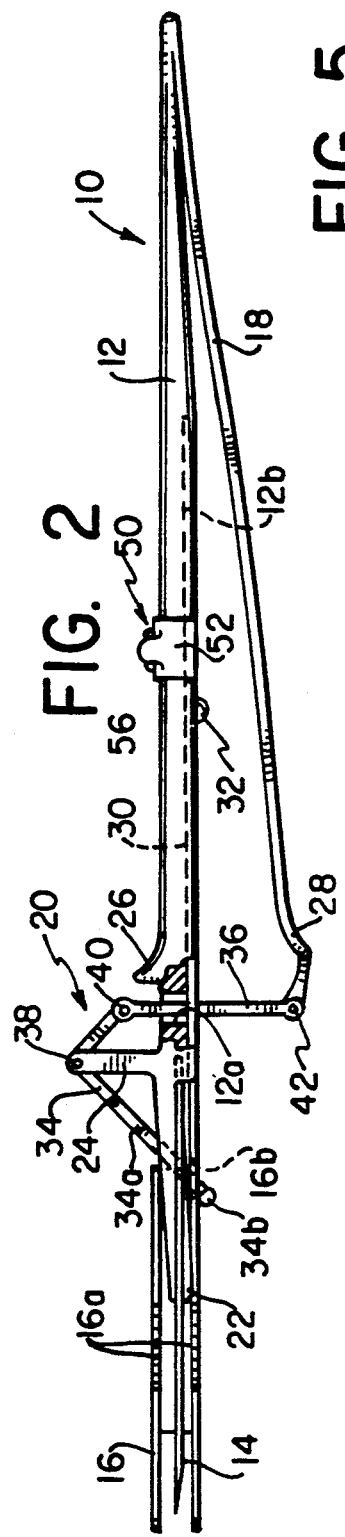
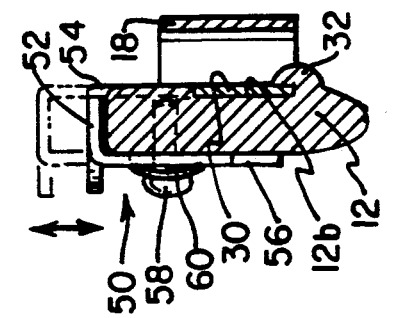
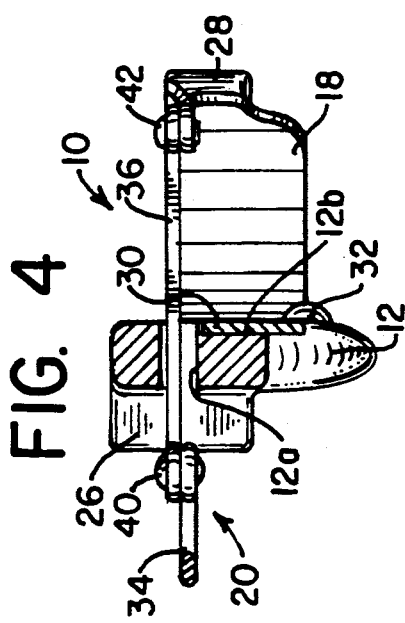
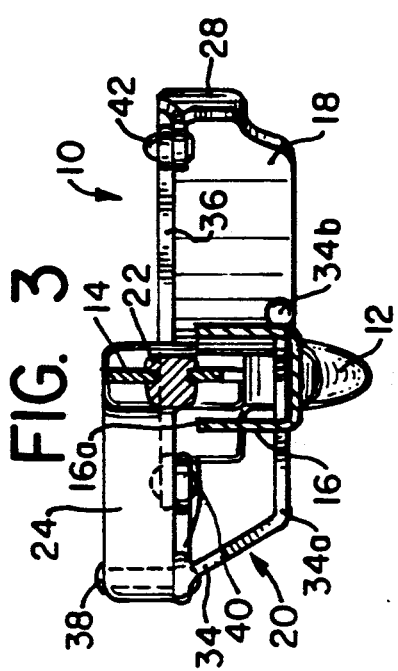

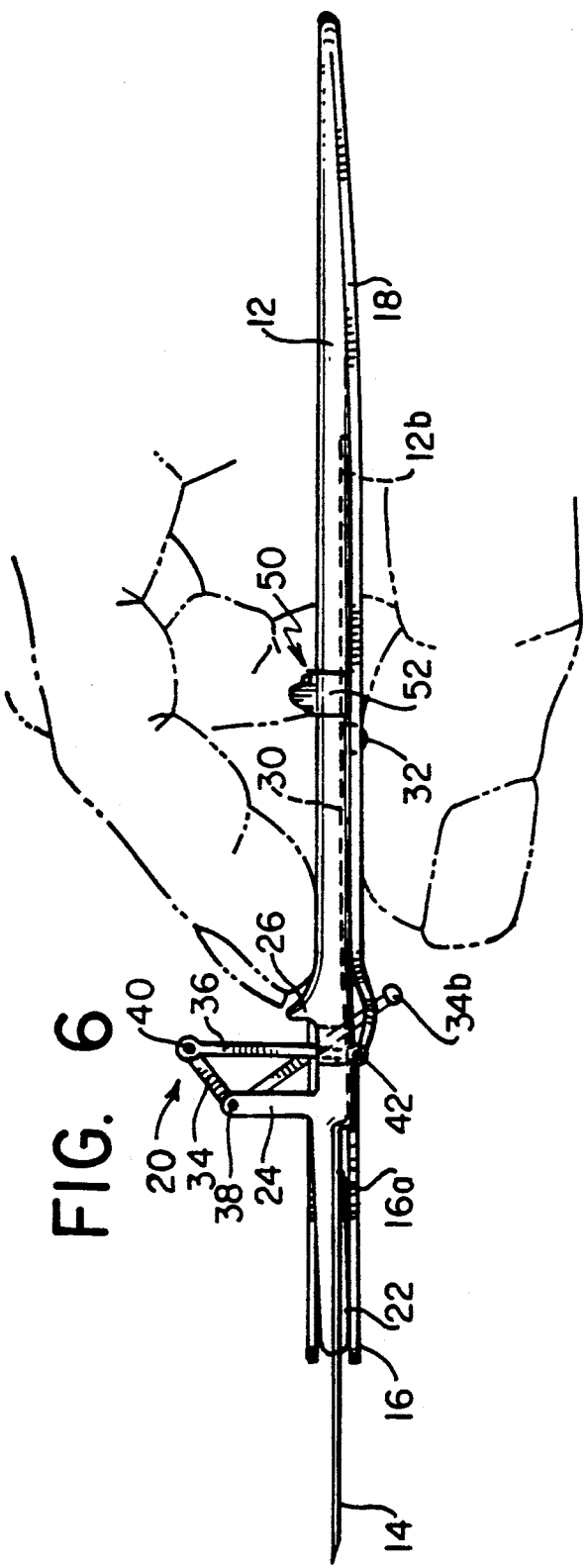
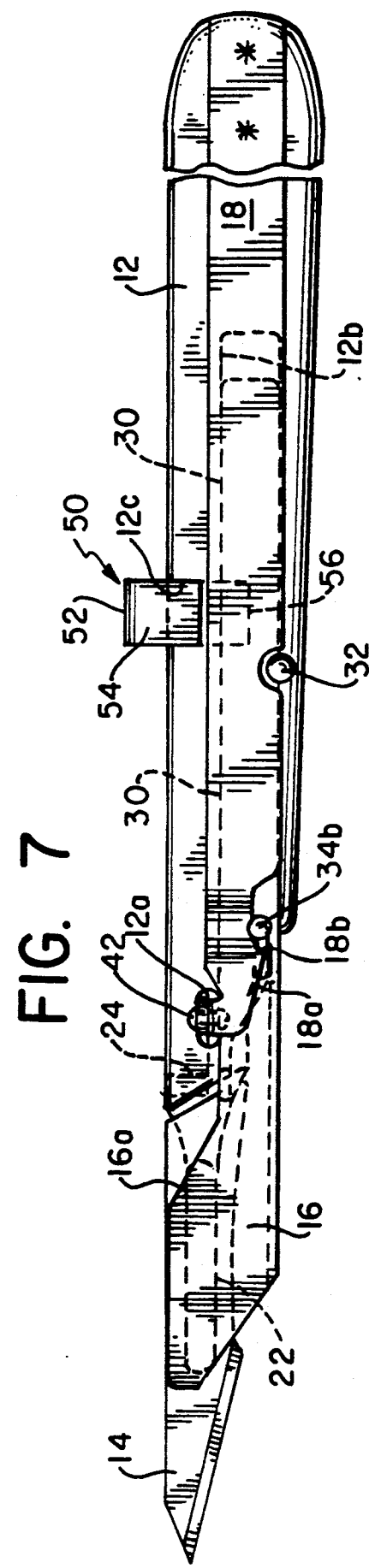

SURGICAL SCALPEL WITH RETRACTABLE BLADE GUARD

FIELD OF THE INVENTION

The present invention relates generally to surgical knives and, more particularly, concerns a surgical scalpel which, in use, automatically moves a protective guard in and out of a protective position over the blade of the knife.

BACKGROUND OF THE INVENTION

Surgical scalpels are a class of knives which are manufactured in accordance with particular stringent standards, in order to assure their quality and precision of handling. It goes without saying that the blade of the knife must be sharp and of the finest quality, but the entire instrument must be of such a weight and size as to fit well and be comfortable within the hand of the surgeon. In addition, it must be well-balanced, to be capable of precise manipulation, and it must be small enough so as not to obstruct the surgeon's view of the blade while in use.

In the sometimes harried atmosphere of an operating room, a surgeon must often work quickly, handing instruments back and forth to assistants. With sharp implements, such as scalpels, the danger of accidental cutting or jabbing of operating room personnel is ever present. Furthermore, certain fatal infections, such as the AIDS virus can be transferred to individuals through minor cuts, when even small quantities of blood are mixed. In a sense, a minor operating room injury can ultimately prove to be fatal.

Scalpels have been provided with removable guards to prevent contact with the blade when not in use. For example, U.S. Pat. No. 4,735,202 issued to R. W. Williams on Apr. 5, 1988 discloses a scalpel in which the blade guard is provided in the form of a sleeve which is slidably mounted over the scalpel and may be locked into position over the blade when not in use. Although such a blade guard could be used effectively prior to starting and after completing a surgical procedure, it could normally not be used and would be of no value during the procedure itself. A primary reason is that two hands are required to position the blade guard, and the surgeon typically has only one hand available for the scalpel during the procedure. Furthermore, even if the surgeon were able to use both hands, the scalpel would be unacceptable, because the surgeon's attention is distracted from the procedure whenever he must handled the scalpel. In addition, the surgeon risks injuring himself with the scalpel every time he must bring his second hand into use. Thus, the scalpel disclosed in this patent would be used in the open position during an entire surgical procedure and, for all intents and purposes, the blade guard is unavailable during the procedure. Various types of utilities knives have been provided with blade guards that slide from a blade-guarded position to a blade-exposed position by manually operating a lever which is coupled to the blade guard so that the pivoting movement of the lever is converted to the sliding movement of the blade guard. Such knives are disclosed in U.S. Pat. No. 4,757,612 issued July 19, 1988 to Peyrot and U.S. Pat. No. 2,380,787 issued July 31, 1945 to Pierce et al. These knives have the advantage that the guard operating lever is operated by the same hand which holds the knife and, therefore, the blade guard may be moved in and out of position in a single-handed operation.

However, such utilities knives are gripped in the hand of the operator in a manner similar to a tennis racket. Surgical scalpels, on the other hand, are held between the fingers delicately, in a manner similar to a pencil. Thus, while the utility knives may be operated in the manner of a bicycle hand brake, the scalpel can only be pressed between the thumb and the forefinger, and the range of manual movement available to operate it is substantially less, on the order of one-quarter to one-half inch. On the other hand, it is essential that the blade guard be moved clear of the scalpel blade when the scalpel is being used, in order that the surgeon's view of the blade be entirely unobstructed. Typically, this requires that the blade guard move over a distance at least as great as an inch. In addition, it is essential that the blade guard be operated without changing position of the hand. That is, the blade guard must be operated while maintaining the hand in the position in which a scalpel is normally held. Otherwise, it could interfere with the surgical procedure. In addition, the pressure required to operate the blade guard should be no greater than the finger pressure required to hold the scalpel, in order to avoid fatigue and cramping of the surgeon's hand.

Broadly, it is an object of the present invention to provide a scalpel with a protective blade guard which can be operated by the hand holding the scalpel so as to move the guard between a blade-guarded and a blade-exposed position. It is specifically intended that the blade guard be so moved when the scalpel is grasped in its position of normal use.

It is another object of the present invention to provide a scalpel with an automatically retractable blade guard which fits well and comfortably within the hand of the surgeon, is capable of precise manipulation, and does not obstruct the surgeon's view of the blade while in use.

It is another object of the present invention to provide a scalpel with a retractable blade guard in which the finger pressure required to retract the guard is comparable to the finger pressure required to hold the scalpel while in use.

It is another object of the present invention to provide a scalpel with a retractable blade guard in which the distance moved by the fingers of the surgeon while moving the blade guard between blade-exposed and blade-guarded positions is substantially less than the distance moved by the blade guard between these positions.

It is also an object of the present invention to provide a scalpel with a retractable blade guard which is simple and convenient in use and relatively inexpensive in construction.

In accordance with the present invention, a scalpel is provided with a blade guard which is mounted for movement between a blade-guarded position and a blade-exposed position and an actuating mechanism for the blade guard is positioned in such a way that the fingers of the surgeon automatically engage the mechanism when the scalpel is held in its normal position of use. The actuating mechanism is coupled to the blade guard through a linkage assembly which causes the blade guard to move over a substantially greater distance than the distance which the surgeon's fingers move in operating the actuating mechanism. In a preferred embodiment, the blade guard slides over a linear path, the actuating mechanism comprises a tongue-like structure integral with the scalpel, and the linkage assembly comprises a plurality of pivotally interconnected lever arms. One of the lever arms is positioned so as to be captured in a detent mechanism when the blade guard is fully retracted to its blade-exposed position.

BRIEF DESCRIPTION OF THE DRAWINGS

The foregoing and further objects, features and advantages of the present invention will be understood more completely from the following detailed description of presently preferred, but nonetheless illustrative, embodiments of the present invention, with reference being had to the accompanying drawings, in which:

FIG. 1 is a right side view of a first embodiment of a scalpel in accordance with the invention, with portions cut away to show structural details, the protective guard being shown in the blade-guarded position;

FIG. 2 is a top view of the scalpel of FIG. 1;

FIG. 3 is sectional view of the scalpel, on an enlarged scale, taken along line 3—3 in FIG. 1 and looking in the direction of the arrows;

FIG. 4 is a sectional view similar to FIG. 3 taken along line 4—4 in FIG. 1 and looking in the direction of the arrows;

FIG. 5 is a sectional view similar to FIG. 3 taken lines 5—5 in FIG. 1 and looking in the direction of the arrows;

FIG. 6 is a top view similar to FIG. 2, showing the scalpel with the protective guard fully retracted to the blade-exposed position;

FIG. 7 is a right-side view similar to FIG. 1 showing the protective guard fully retracted;

DETAILED DESCRIPTION OF THE PREFERRED EMBODIMENTS

Figure 8:
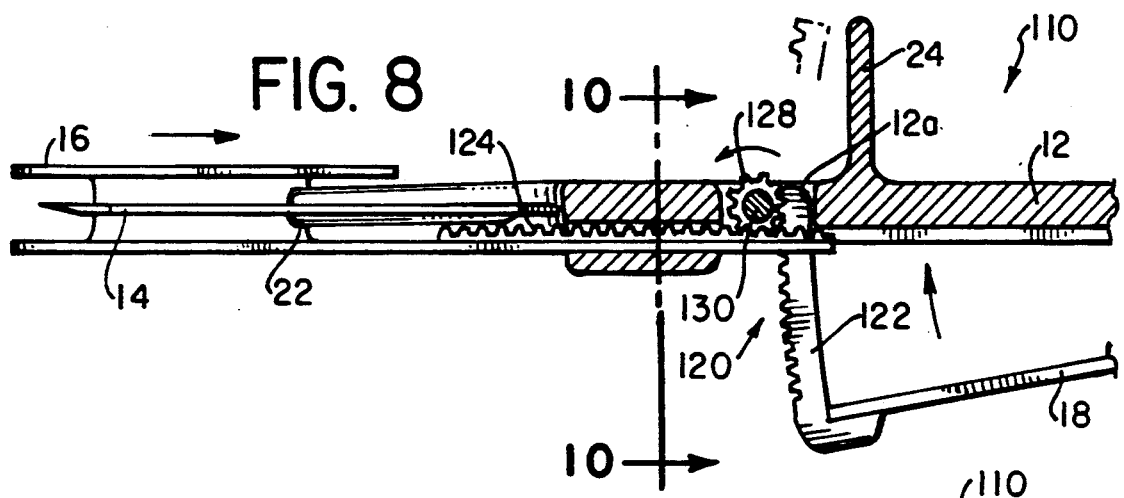
FIG. 8 is a fragmentary top view of a second embodiment of a scalpel in accordance with the present invention, with portions shown in sections, to facilitate description of structural details.

Turning now to the details of the drawings, FIGS. 1-7 illustrate a preferred embodiment 10 of a scalpel embodying the present invention. Scalpel 10 broadly comprises: a handle or holder 12; a blade 14 detachably secured to handle 12; a blade guard 16 acting as a protective sheathe for blade 14; an actuating arm 18; and a linkage assembly 20 connecting the actuating arm 18 with the blade guard 16.

In use, the scalpel is operated by being held in the hand and depressing the actuating arm 18 towards body 12. Such movement is coupled through the linkage assembly 20 to the blade guard 16, causing it to slide backwards to expose the blade 14 (compare FIGS. 2 and 6). As can be seen in FIG. 6, when the blade 14 is fully exposed, scalpel 10 is held in the hand in the normal position of use.

Handle 12 is preferably made of high quality stainless steel, although it could equally well be made of any other material which is used for surgical knives. Actuating arm 18 is preferably made of the same material and is formed integrally with handle 12. By arching actuating arm 18 outward slightly, it cooperates with handle 12 to form a tong-like structure. The inherent resilience of the actuator arm will ensure that it returns to the position shown in FIG. 2 upon being released. At its forward end, arm 12 is fashioned with a fitting 22 to detachably receive and retain the blade 14. This fitting is preferably of a standard type, so that the conventional blades of various shapes and sizes may be interchanged.

At a distance behind the blade fitting 22, handle 12 is provided with a laterally projecting supporting post 24 for the linkage assembly 20. Behind post 24, there is provided a bore 12a which passes entirely through ;arm 12. Immediately behind bore 12a, arm 12 is formed with a slight outwardly flared projection 26 which serves as a finger rest, and the actuating arm 18 is correspondingly flared at 28 to form a similar finger rest. In addition, the under surface at the forward end of arm 18 is formed with an abruptly terminating ramp portion 18a (see FIG. 7), to define a detenting mechanism, to be discussed in detail below.

Blade guard 16 is also preferably made of stainless steel, and its finish preferably matches the finish of handle 12 and actuating arm 18. As can be seen in FIG. 3, the forward end of guard 16 is preferably formed into a U-shaped channel, so as to cover all sharp portions of the blade. This protective portion of guard 16 is preferably formed with a cut out 16a near the rear of the blade guard (See FIG. 7), so as to avoid interference with arm 24 and the mechanical linkage 20. In addition,, a slit 16b is provided near the bottom of guard 16 behind cut-out 16a. At its rear, guard 16 is formed into a thin, elongated rail 30, which extends rearwardly for a substantial distance. Handle 12 is formed with a shallow groove 12b, which receives rail 30 with a close, free-sliding tolerance and serves as a guideway therefore. Rail 30 is retained within groove 12b by means of a rivet 32, or the like. Alternatively, handle 12 could be formed with any type of element affixed below groove 12b which overlaps rail 30 so as to retain it.

The linkage assembly 20 includes a generally L-shape arm 34 and a straight arm 36. The L-shape arm is pivotally mounted to post 24 at 38. A pivotable connection 40 is provided between arms 34 and 36, and a similar pivotable connection 42 is provided between arm 36 and actuating arm 18. As can be seen in FIG. 3, the longer leg of L-shape arm 34 is not formed in a single plane, but, in fact, includes a bend at 34a, so as to form an angle in a plane perpendicular to the L-shape (see FIG. 3). Arm 36 extends through aperture 12a in handle 12, and the longer leg of arm 34 extends through slit 16b in guard 16. The free end of arm 34 is formed into a ball shape 34b, or the like, to prevent it from accidentally pulling out of slot 16b.

The scalpel 10 also includes a safety lock 50, which prevents blade guard 16 from being retracted. The scalpel may then be handled safely, without the danger of accidentally uncovering the blade and causing injury. Safety lock 50 includes a slide member 52 having a generally inverted U-shape. The right hand leg 54 of slide member 52 extends into a channel 12c in handle 12, which channel is an extension of channel 12b. The left hand leg 56 of slide member 52 includes a vertical slot 56a, which permits the slide member 52 to be secured to handle 12 by means of a rivet 58 and a resilient washer 60.

In operation, the vertical slot 56a permits slide member 52 to be translated vertically with respect to arm 12 from a locked position (shown in FIG. 1 and in solid lines in FIG. 5) to an unlocked position (shown in FIG. 7 and in broken lines in FIG. 5). Rivet 58 and washer 60 assure that member 52 will be retained in the selected position as a result of increased friction. In the locked position, leg 54 is interposed in groove 12b behind rail 30, so that blade guard 16 cannot slide backwards. When slide member 52 is moved to its unlocked or raised position, arm 54 is withdrawn from behind rail 30, so that the plate guard 16 may be retracted. It is contemplated that the safety lock 50 would normally be in its locked position, until the surgeon is prepared to use scalpel 10. At that time, the safety lock 50 would be unlocked, to permit the blade guard 16 to be moved freely in and out of the blade-guarded position.

From the above description, it will be appreciated that when the scalpel 10 is grasped in the user's hand in the position of normal use, actuating arm 18 will be forced towards handle 12, as shown in FIG. 6. Inasmuch as actuating arm 18 is coupled to the shorter leg of arm 34 (the shorter leg is substantially shorter and preferably ⅛ to ½ the length of the longer leg), actuating arm 18 is moved over a substantially shorter distance than the distance over which blade guard 16 slides in exposing the blade (compare FIGS. 2 and 6). As will be appreciated from FIGS. 6 and 7, as the blade guard 16 moves rearward, the longer leg of arm 34 slides downwardly along the inclined surface 18a on arm 18 and is ultimately captured behind the abrupt edge 18b, which forms a detent mechanism. The inherent resilience in arm 34 then holds it in position and prevents the blade guard from sliding forward. When the surgeon has completed using the scalpel, he simply applies a slight downward force to ball end 34b. This frees the longer leg of arm 34 from the detent 18b, and the inherent resilience of arm 18 pulls it away from handle 12, pulling arm 36 with it. As a result, arm 36 causes arm 34 to rotate in a clockwise direction, and blade guard 16 is returned to its blade-guarded position.

Figure 9:
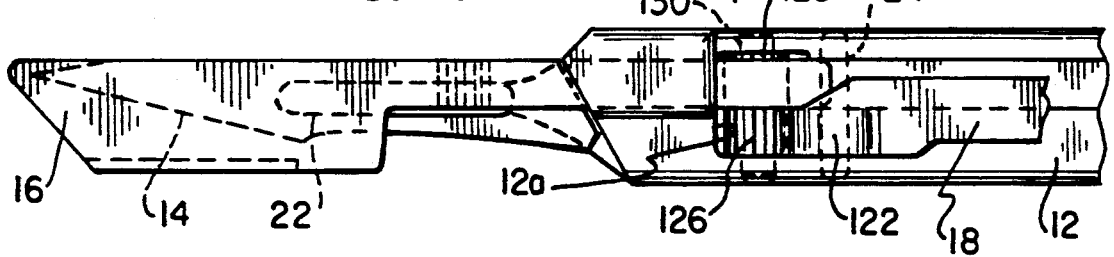
FIG. 9 is fragmentary right-side view of the scalpel in FIG. 8.
Figure 10:
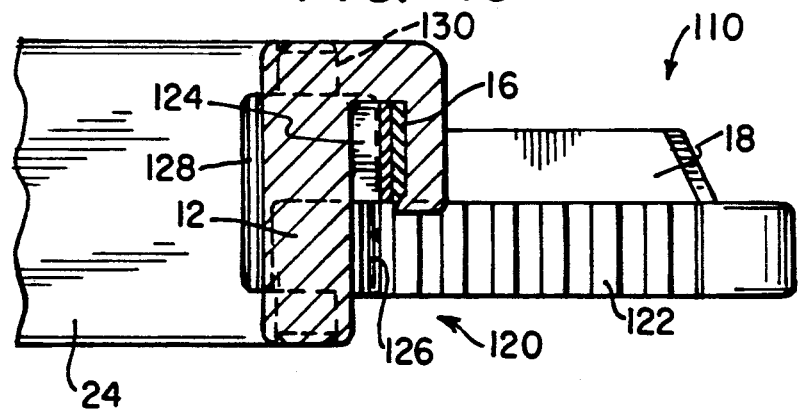
FIG. 10 is a fragmentary sectional view, on an enlarged scale, taken along lines 10—10 in FIG. 8 and looking in direction of the arrows.

Referring now to FIGS. 8–10, there is disclosed a second embodiment 110 of a scalpel in accordance with the present invention. In this embodiment, and all other embodiments that follow, elements which are essentially the same as the corresponding elements in embodiment 10 are indicated with the same reference characters and will not be described any further. Scalpel 110 differs from scalpel 10 essentially in the specifics of the linkage assembly, which is here indicated by the reference character 120. This linkage assembly includes an arcuate rack element 122 projecting laterally from actuating arm 18 and through an opening in handle 12. A linear rack element 124 is provided on the inner surface of blade guard 16. In addition, there is provided a lower pinion 126 which meshes with rack 122 and an upper pinion 128 which meshes with rack 124. Pinions 126 and 128 are mounted on a common axle 130 so as to rotate together, and the ratio between the number of teeth on the respective pinions is selected so that rack 124 will move a substantially greater distance than rack 122. The manner of using the scalpel 110 and its overall operation will be essentially the same as scalpel 10.

Figure 11:
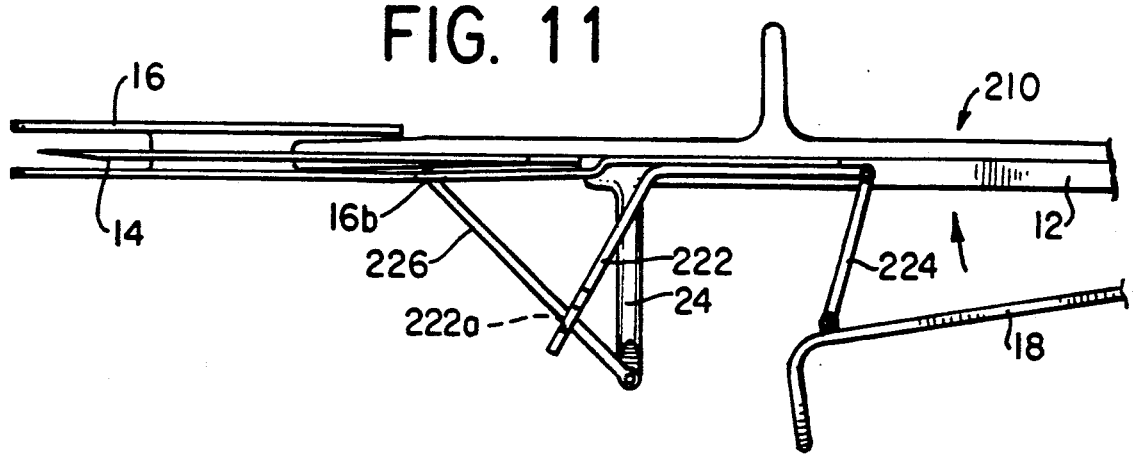
FIG. 11 is a fragmentary top view of a third embodiment of a scalpel in accordance with the present invention.
Figure 12:
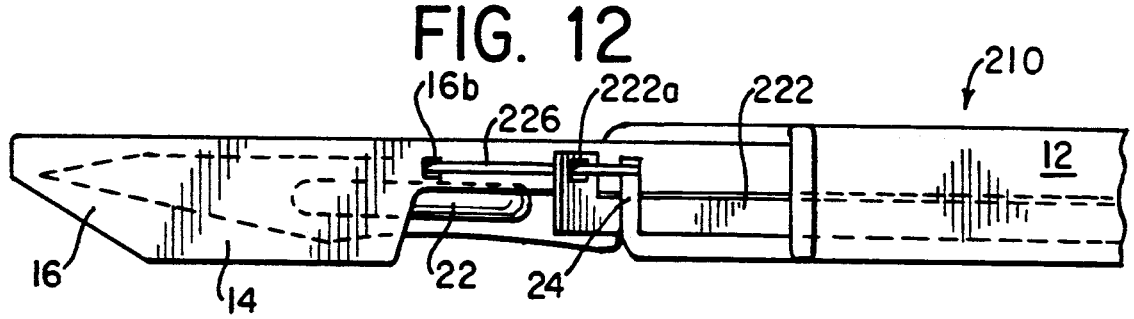
FIG. 12 is a right-side view of the scalpel of FIG. 11.

FIGS. 11 and 12 illustrate a third embodiment 210 of a scalpel in accordance with the present invention. Again, the difference in this embodiment resides in the linkage assembly, now indicated as 220. This linkage assembly includes a shuttle member 222 which is slidably mounted on handle 12. Shuttle member 222 is connected to actuating arm 18 through an arm 224, which is pivotally mounted to both the actuating arm 18 and the angle member 222. An arm 226 is pivotally mounted to post 24 at one end, and the other end of the arm extends through a slot 222a in shuttle member 222 and a slot 16b in blade guard 16.

In operation, urging actuating arm 18 towards body 12 causes arm 224 to pivot with respect to shuttle member 222, which is forced to slide rearwardly. As shuttle member 222 moves rearwardly, it causes arm 226 to pivot in a clockwise direction, drawing blade guard 16 rearwardly. When actuating arm 18 is released, its resilience causes the reverse movement, and blade guard 16 is returned to its blade-guarded position.

Figure 13:
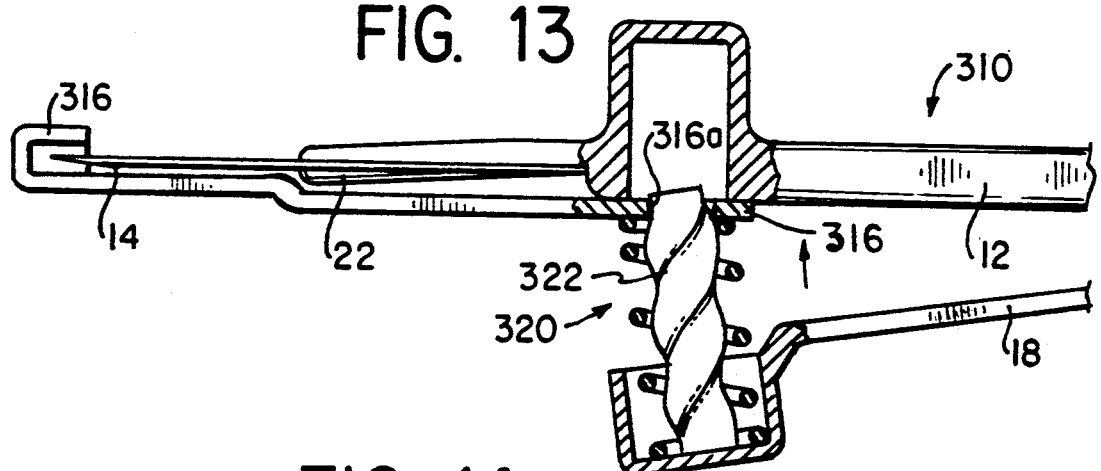
FIG. 13 is a fragmentary top view of a fourth embodiment of a scalpel in accordance with the invention.
Figure 14:
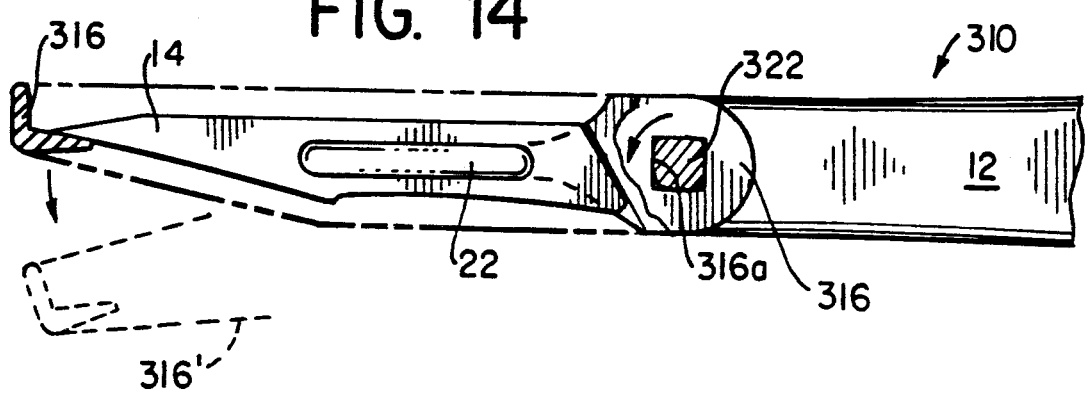
FIG. 14 is a right-side of the scalpel of the FIG. 14, with the acuating arm mechanism removed.

FIGS. 13 and 14 illustrate a fourth embodiment 310 of a scalpel in accordance with the present invention. As indicated schematically in phantom image 316', in the present embodiment, the blade guard 116 rotates so as to expose the blade 14. In scalpel 310, linkage assembly 320 includes a shaft 322 which extends inwardly from actuating arm 18 towards handle 12. Shaft 322 is formed by axially twisting a rod with a square cross section. This produces a spiral distortion of the rod. Blade guard 316 is rotatably mounted to handle 12 and includes a square hole 316a, which conforms in size to the cross-section of shaft 322.

In operation, as actuating arm 18 is forced towards handle 12, shaft 322 is pressed into hole 316a, and blade guard 316 rotates, in order to follow the spiral distortion of the shaft. By design, blade guard 316 is rotated approximately 180° to the blade-exposed position when actuating arm 18 is fully depressed. With the blade 14 exposed, the scalpel may be used in the normal manner. When actuating arm 18 is released, the resilience of the arm and a helping spring 324 force shaft 322 away from handle 12, causing blade guard 316 to return to its blade-guarded position. In the present embodiment, the magnified movement of blade guard 316 as compared to the actuating shaft is achieved through the rotation of the blade guard.

Although preferred embodiments of the invention have been disclosed for illustrative purposes, those skilled in the art will appreciate that various modifications, additions and substitutions are possible, without departing from the scope and spirit of the invention as disclosed in the accompanying claims.

We claim:

1. A scalpel comprising:
   an elongated handle having front and rear ends;
   a substantially planar surgical blade secured at the front end of said handle, said blade having a direction of cut extending along the length of the handle;
   actuating means disposed in a position to be engaged by the fingers of a user when holding the scalpel in a position of normal use and mounted for movement generally perpendicular to the plane of said blade and the direction of cut thereof relative to said handle;
   a blade guard constructed to cover at least any sharp portions of said blade and mounted for movement between a blade-guarded position in which said blade is covered and a blade-exposed position in which said blade may be used for cutting; and linkage means for coupling the movement of said actuating means to said blade guard so as to move the same between said blade-guarded and blade-exposed positions, said linkage means including means for causing the amount of movement of said blade guard to be substantially greater than the amount of movement of said actuating means.

2. A scalpel in accordance with claim 1 wherein said actuating means comprises a resilient actuating arm mounted at the rear of said handle so that a forward portion of said actuating arm is at a distance from said handle, whereby said actuating arm and said handle cooperate in the manner of a pair of tongs, said linkage means being connected to the forward end of said actuating arm.

3. A scalpel in accordance with claim 1 wherein said blade guard is mounted for sliding movement along said handle.

4. A scalpel in accordance with claim 1 wherein said linkage means comprises first rack means coupled to be moved by movement of said actuating means, second rack means on said blade guard, and pinion means for coupling movement of said first rack means to said second rack means so that the amount of movement of said second rack means is substantially greater than the amount of movement of said first rack means.

5. A scalpel in accordance with claim 4 wherein said actuating means comprises a resilient actuating arm mounted at the rear of said handle so that a forward portion of said actuating arm is at a distance from said handle, whereby said actuating arm and said handle cooperate in the manner of a pair of tongs, said linkage means being connected to the forward end of said actuating arm.

6. A scalpel in accordance with claim 5 wherein said blade guard is mounted for sliding movement along said handle.

7. A scalpel in accordance with claim 4 wherein said blade guard is mounted for sliding movement along said handle.

8. A scalpel in accordance with claim 4 wherein said pinion means comprises a first pinion meshed with said first rack means, a second pinion meshed with said second rack means and means coupling said first and second pinions for rotation together, the ratio of the number of teeth between said first and second pinions being selected to achieve substantially greater movement of said second rack means than said first rack means.

9. A scalpel in accordance with claim 1 further comprising locking means mounted on said handle for adjustment relative to said handle so as to prevent movement of said blade guard from said blade-guarded position to said blade-exposed position, said locking means being also adjustable to permit free movement of said blade guard between said blade-guarded and said blade-exposed positions.

10. A scalpel comprising:
a handle having front and rear ends;
a surgical blade secured at the front end of said handle;
actuating means disposed in a position to be engaged by the fingers of a user when holding the scalpel in a position of normal use and mounted for movement relative to said handle;
a blade guard constructed to cover at least any sharp portions of said blade and mounted for movement between a blade-guarded position in which said blade is covered and a blade-exposed position in which said blade may be used for cutting, said blade guard being mounted for sliding movement along said handle; and linkage means for coupling the movement of said actuating means to said blade guard so as to move the same between said blade-guarded and blade-exposed positions, said linkage means being constructed so that the amount of movement of said blade guard is substantially greater than the amount of movement of said actuating means; said linkage means comprising an L-shaped arm having one leg of said L substantially shorter than the other, the vertex of said L-shaped arm being mounted for pivotal movement with respect to said handle at a distance laterally thereof, the shorter leg of said L-shaped arm being coupled to receive the movement of said actuating means and the longer leg of said arm being connected to said blade guard so as to impart a sliding movement thereto when said L-shaped arm is pivoted.

11. A scalpel in accordance with claim 10 wherein said actuating means comprises a resilient actuating arm mounted at the rear of said handle so that a forward portion of said actuating arm is at a distance from said handle, whereby said actuating arm and said handle cooperate in the manner of a pair of tongs, said linkage means being connected to the forward end of said actuating arm.

12. A scalpel in accordance with claim 10 further comprising detent means for capturing a portion of one of said L-shaped arm and said actuating arm when said blade is in its blade-exposed position.

13. A scalpel comprising:
a handle having front and rear ends;
a surgical blade secured at the front end of said handle;
actuating means disposed in a position to be engaged by the fingers of a user when holding the scalpel in a position of normal use and mounted for movement relative to said handle;
a blade guard constructed to cover at least any sharp portions of said blade and mounted for movement between a blade-guarded position in which said blade is covered and a blade-exposed position in which said blade may be used for cutting; and
linkage means for coupling the movement of said actuating means to said blade guard so as to move the same between said blade-guarded and blade-exposed positions, said linkage means being constructed so that the amount of movement of said blade guard is substantially greater than the amount of movement of said actuating means; said linkage means
comprising
a first arm having a first end mounted for pivotal movement relative to said handle at a distance laterally thereof and a second end connected to said blade guard so as to couple pivotal movement of said first arm as sliding movement of said blade guard;
shuttle means mounted for sliding movement along said handle;
means coupling said actuating means to said shuttle means for converting the movement of said actuating means to sliding movement of said shuttle means; and means coupling said shuttle means to said first arm for converting the sliding movement of said shuttle means to proportionate rotational movement of said arm.

14. A scalpel in accordance with claim 13 wherein said actuating means comprises a resilient actuating arm mounted at the rear of said handle so that a forward portion of said actuating arm is at a distance from said handle, whereby said actuating arm and said handle cooperate in the manner of a pair of tongs, said linkage means being connected to the forward end of said actuating arm.

15. A scalpel in accordance with claim 14 wherein said blade guard is mounted for sliding movement along said handle.

16. A scalpel in accordance with claim 13 wherein said blade guard is mounted for sliding movement along said handle.

17. A scalpel in accordance with claim 13 wherein said blade guard is mounted for rotational movement relative to said handle, said linkage means comprising means for converting the movement of said actuating means to proportionate rotational movement of said blade guard.

18. A scalpel in accordance with claim 17 wherein said actuating means comprises a resilient actuating arm mounted at the rear of said handle so that a forward portion of said actuating arm is at a distance from said handle, whereby said actuating arm and said handle cooperate in the manner of a pair of tongs, said linkage means being connected to the forward end of said actuating arm.

19. A scalpel in accordance with claim 17 wherein said coupling means comprises a rod having a polygonal cross sectional shape extending between said actuating arm and said blade guard, said blade guard having an aperture therein conforming in shape and size to the cross section of said rod, said rod having been axially twisted so as to impart of permanent spiral distortion thereto.

20. A method for automatically guarding and exposing the substantially planar blade of a surgical scalpel having an elongated handle and a direction of cut extending along the length of the handle comprising the steps of:

providing a blade guard over said blade which is mounted so as to be moved from a blade-guarded position to a blade-exposed position;

positioning an actuating member on said scalpel so as to be moved generally perpendicular to the plane of the blade and the direction of cut by the fingers of a user when the scalpel is grasped for normal use; and coupling the actuator member movement to said blade guard so that the blade guard is moved over a substantially greater distance than said actuating member.

* * * * *